United States Patent
Yang

(10) Patent No.: US 11,065,190 B2
(45) Date of Patent: Jul. 20, 2021

(54) COSMETIC COMPOSITION COMPRISING SOLUBILIZED PIGMENT AND METHOD FOR PREPARING THE SAME

(71) Applicant: AMOREPACIFIC CORPORATION, Seoul (KR)

(72) Inventor: Keunyong Yang, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 17/007,722

(22) Filed: Aug. 31, 2020

(65) Prior Publication Data
US 2021/0077373 A1    Mar. 18, 2021

(30) Foreign Application Priority Data

Sep. 16, 2019  (KR) .......................... 10-2019-0113532

(51) Int. Cl.
| | |
|---|---|
| A61K 8/46 | (2006.01) |
| A61K 8/81 | (2006.01) |
| A61Q 1/02 | (2006.01) |
| A61Q 1/04 | (2006.01) |
| A61Q 1/06 | (2006.01) |

(52) U.S. Cl.
CPC ............ *A61K 8/466* (2013.01); *A61K 8/8147* (2013.01); *A61Q 1/02* (2013.01); *A61K 2800/48* (2013.01); *A61Q 1/04* (2013.01); *A61Q 1/06* (2013.01)

(58) Field of Classification Search
None
See application file for complete search history.

(56) References Cited

U.S. PATENT DOCUMENTS

| | | | |
|---|---|---|---|
| 6,063,391 A | * | 5/2000 | Nanba .................... A61K 8/585 424/407 |
| 2004/0009294 A1 | | 1/2004 | Kuribayashi et al. |
| 2005/0069704 A1 | | 3/2005 | Rathschlag et al. |
| 2005/0129637 A1 | | 6/2005 | Aota |

(Continued)

FOREIGN PATENT DOCUMENTS

| | | |
|---|---|---|
| JP | 2004-010834 A | 1/2004 |
| JP | 2004-043776 A | 2/2004 |

(Continued)

OTHER PUBLICATIONS

MS Kim, SI Seok, BY Ahn, SM Koo, SU Paik. "Encapsulation of Water-Soluble Dye in Spherical Sol-Gel Silica Matrices." Journal of Sol-Gel Science and Technology, vol. 27, 2003, pp. 355-361. (Year: 2003).*

(Continued)

*Primary Examiner* — Isaac Shomer
(74) *Attorney, Agent, or Firm* — Sughrue Mion, PLLC

(57) ABSTRACT

One aspect of the present disclosure is a cosmetic composition containing a solubilized pigment and a method for preparing the same. More specifically, the cosmetic composition containing the solubilized pigment may be prepared through a process of dissolving a pigment in an aqueous phase by dispersing the pigment in the aqueous phase using a pigment dispersing thickener and stabilizing by further increasing the viscosity using a stabilizing thickener. Since the solubilized pigment exhibits dyeing properties similar to dyes, it can be widely applied to various cosmetic compositions.

8 Claims, 2 Drawing Sheets

(56) References Cited

U.S. PATENT DOCUMENTS

| | | | | |
|---|---|---|---|---|
| 2006/0008489 A1* | 1/2006 | Egawa | ..................... | A61K 8/39 |
| | | | | 424/401 |
| 2012/0014885 A1* | 1/2012 | Collier | ..................... | A61Q 9/00 |
| | | | | 424/59 |
| 2014/0288191 A1* | 9/2014 | Kim | ......................... | A61K 8/73 |
| | | | | 514/772.4 |
| 2016/0310374 A1* | 10/2016 | Debeaud | .............. | A61Q 19/001 |

FOREIGN PATENT DOCUMENTS

| | | |
|---|---|---|
| JP | 2005-120368 A | 5/2005 |
| JP | 2009-161439 A | 7/2009 |
| JP | 5009547 B2 | 8/2012 |
| KR | 10-2014-0054576 A | 5/2014 |
| KR | 10-1771421 B1 | 8/2017 |
| KR | 10-1957585 B1 | 3/2019 |
| WO | 2018/056608 A1 | 3/2018 |

OTHER PUBLICATIONS

Mintel; "Lip Mask", Database GNPD, XP055771987, Apr. 8, 2016, [Online] Database accession No. 3915645 (2 pages total).

Mintel; "Light Liquid Foundation", Database GNPD, XP055772002, Nov. 11, 2008, [Online] Database accession No. 1002787 (6 pages total).

Mintel; "Heartbeats Hydrated Lustrous Lip Tint", Database GNPD, XP055772024, Jan. 16, 2018, [Online] Database accession No. 5383079 (4 pages total).

* cited by examiner

[FIG. 1]
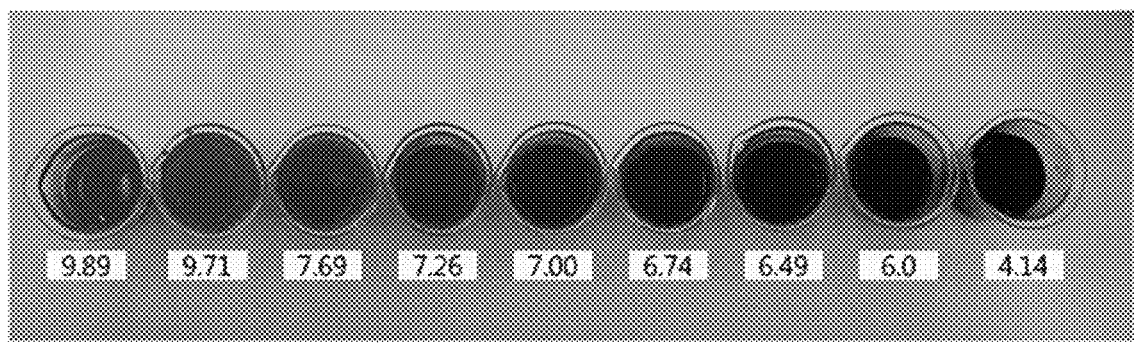
[FIG. 2]
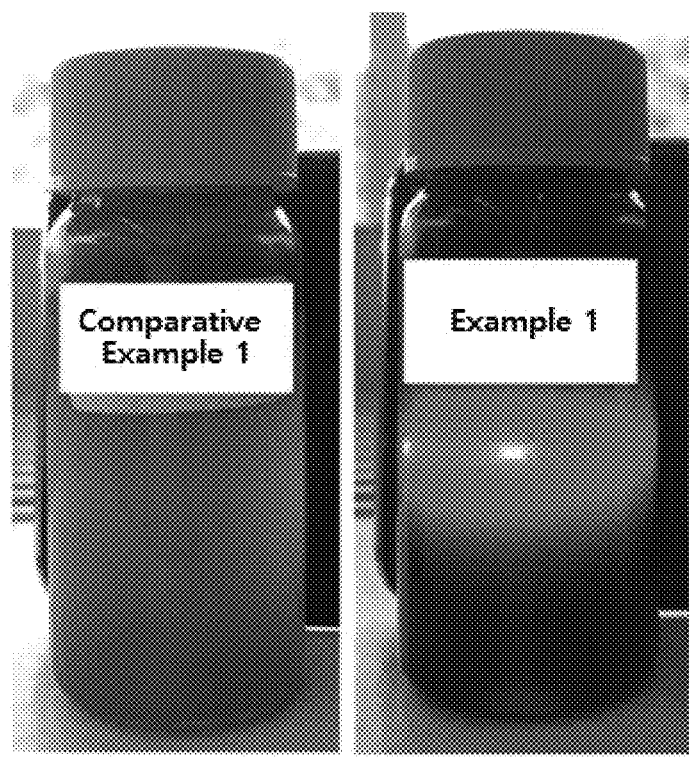

[FIG. 3]
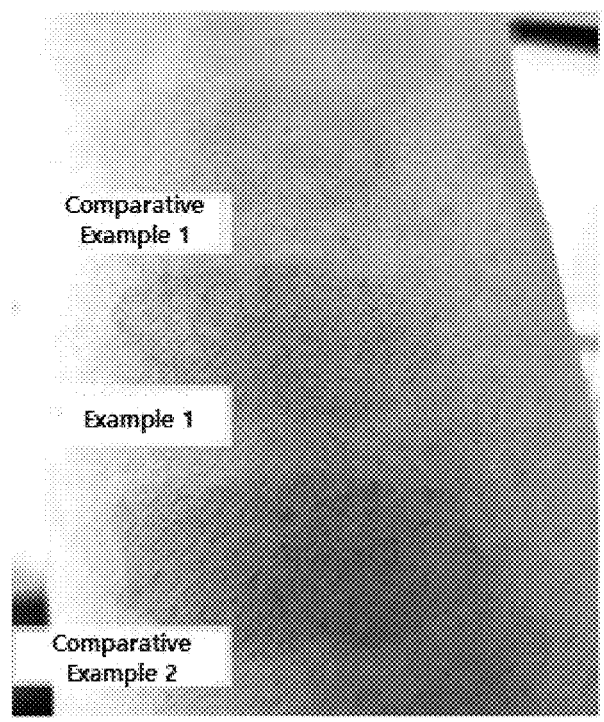

COSMETIC COMPOSITION COMPRISING SOLUBILIZED PIGMENT AND METHOD FOR PREPARING THE SAME

CROSS-REFERENCE TO RELATED APPLICATION

This application claims under 35 U.S.C. § 119(a) the benefit of Korean Patent Application No. 10-2019-0113532 filed on Sep. 16, 2019, the entire contents of which are hereby incorporated by reference.

BACKGROUND

(a) Technical Field

One aspect of the present disclosure relates to a cosmetic composition comprising a solubilized pigment and a method for preparing the same.

(b) Background Art

In general, makeup cosmetics are used for the purpose of concealing defects on the skin by using pigments, giving a beautiful color, and protecting the skin from UV rays. In addition, the makeup cosmetics containing the pigments are also used for ancillary purposes of providing psychological stability through skin beautification and skin protection functions.

In the makeup cosmetic, formulations such as an emulsifying type, a dispersing type, or a powder type have some differences depending on their forms, but as a representative pigment for the application of color and the defects on the skin, titanium dioxide ($TiO_2$), a white pigment, is the most used. However, in the case of titanium dioxide that has not been surface-modified, the more excellent the ability to conceal defects on the skin, the more re-agglomeration occurs. Thus, after makeup, it causes the agglomeration phenomenon, and in particular, its structure is tetrahedral, which damages the skin when applied to the skin, and its malleability and ductility are very bad, which is a factor that degrades usability.

In order to overcome these disadvantages, there are developing methods for coating or complexing the surface of the pigment with various materials. Conventionally, the pigment was surface-treated with silicon, fluorine, amino acids, chitosan, metal salts, etc. to improve adhesion and durability. However, the surface-treated pigments still exhibit an unsatisfactory effect in preventing the spreadability in the formulation, the re-agglomeration and the cosmetic collapse during use or after a lapse of time.

Also, in general, the pigment is insoluble, so the color is expressed when applied, thereby resulting in an opaque and strong color, but there is a disadvantage that the persistence is inferior and it is dispersed only in the oil phase.

In addition, dyes are soluble in a solvent, and the color is expressed by dyeing to show a transparent and natural color, but due to restrictions on dyes that can be used in cosmetics, the types of dyes that can be used in cosmetics are extremely limited. Accordingly, there are ongoing studies to stably apply an insoluble pigment to cosmetics.

For example, a low-viscosity cosmetic composition with a luxurious appearance has been developed. This is a cosmetic composition that solves the problem of pigment separation at low viscosity by mixing an organic acid with the pigment. However, since the pigment is simply dispersed and not solubilized, there is a problem that the cosmetic composition does not last long after application on skin of a user.

In addition, an aqueous dispersion type makeup cosmetic composition has been developed. This is characterized by mixing a thickener with the pigment to improve the dispersibility of the pigment, thereby improving the spreadability, adhesion, moisturizing feeling, and glossy. However, even in this case, since the pigment is simply dispersed and not solubilized, there is a problem that the cosmetic composition does not last long after application on skin of a user.

As described above, there have been studies to stably apply the soluble pigment to the cosmetic composition, but the performance of the solubilization of the pigment and the application to the cosmetic composition is still insufficient.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

Accordingly, the inventors of the present invention have conducted various studies to solve the above problems, and as a result, have developed a cosmetic composition comprising a solubilized pigment by mixing a pigment dispersing thickener with a pigment showing insoluble, dispersing the pigment in an aqueous phase and then acidifying and dissolving it, and then mixing a stabilizing thickener to increase the viscosity to the actual usable level.

Therefore, it is an object of one aspect of the present disclosure to provide a cosmetic composition comprising a solubilized pigment and a method for preparing the same.

In order to achieve the above object, one aspect of the present disclosure provides a cosmetic composition comprising a solubilized pigment, which comprises a pigment; a pigment dispersing thickener; an acid; and a stabilizing thickener.

Another aspect of the present disclosure provides a method for preparing a cosmetic composition comprising a solubilized pigment, which comprises the steps of (S1) dispersing a pigment in an aqueous phase by adding the pigment and a pigment dispersing thickener to the aqueous phase;

(S2) dissolving the pigment in the aqueous phase by adding an acid to the aqueous phase in which the pigment is dispersed; and (S3) stabilizing by adding a stabilizing thickener to the aqueous phase in which the pigment is dissolved.

The solubilized pigment according to one aspect of the present disclosure can be modified to have hydrophilicity by an acid and thus dissolved in an aqueous phase formulation.

In addition, the solubilized pigment has properties similar to dyes, for example, a transparent color and thus has a dyeing affinity, so that color can be expressed by dyeing to exhibit a transparent and natural color.

In addition, the soluble pigment may exhibit a color different from red-based dyes usable for lip cosmetics, while exhibiting properties similar to dyes.

In addition, the soluble pigment can be applied universally without any restrictions due to international regulations compared to other dyes, and thus can be widely used in various cosmetic compositions.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein:

FIG. 1 is a photograph showing the color of the pigment depending on the pH controlled by the acid added to the aqueous phase solvent in which the pigment is dispersed in Example 1.

FIG. 2 is a photograph showing the appearances of the cosmetic compositions for lips prepared in Example 1 and Comparative Example 1, respectively.

FIG. 3 is a photograph showing the experimental results of dyeing affinity of the cosmetic compositions prepared in Example 1, Comparative Example 1 and Comparative Example 2, respectively.

It may be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The terms and words used in the present specification and claims may not be construed as limited to ordinary or dictionary meanings, and may be construed in a sense and concept consistent with the technical idea of the present invention, based on the principle that the inventor can properly define the concept of a term to describe his invention in the best way possible.

As used herein, the term "pigment" refers to a general insoluble pigment, and thus refers to a kind of organic synthetic coloring agent having an opaque color and a non-dyeing affinity. That is, although the pigment is dispersed in the formulation and exhibits a vivid and opaque color, since it has a hydrophobicity, it is not easy to disperse in an aqueous phase formulation. In addition, since the pigment is coated on the surface of the skin when applied to the surface of the skin, it has a property of being easily removed when wiped off.

The term "dye" as used herein refers to an organic synthetic coloring agent having a transparent color and dyeing affinity. That is, the dye exhibits a transparent color when dissolved in a solvent, and the dye has a property of being stained on the surface of the skin when applied to the surface of the skin and not removed even when wiped off. However, the dye has limitations due to international regulations, which limits its application.

The term "solubilized pigment" as used herein has a transparent color and dyeing affinity, and thus exhibits properties similar to dyes. That is, the solubilized to pigment has a hydrophilicity and thus is easy to disperse in an aqueous phase formulation and exhibits a color that is differentiated from red-based dyes usable in general color cosmetics. In addition, the solubilized pigment exhibits similar properties to dyes, but has no restrictions due to international regulations as compared to dyes, and thus can be applied universally.

As used herein, the term "pigment dispersing thickener" is a thickener capable of dispersing a pigment, that is, an insoluble pigment in an aqueous phase solvent, which can disperse the pigment in the aqueous phase solvent by increasing the aqueous phase solvent to a low viscosity. In this specification, the pigment dispersing thickener may be referred to as a first thickener.

The term "stabilizing thickener" as used herein refers to a thickener capable of forming a generally usable cosmetic composition formulation by increasing the viscosity of the aqueous phase solvent in which the pigment is solubilized and dissolved by the pigment dispersing thickener and an acid. In this specification, the pigment dispersing thickener may be also referred to as a second thickener.

Cosmetic Composition Containing Solubilized Pigment

One aspect of the present disclosure relates to a cosmetic composition comprising a solubilized pigment, wherein the cosmetic composition comprising the solubilized pigment comprises a pigment; a pigment dispersing thickener; an acid; and a stabilizing thickener.

The cosmetic composition comprising the solubilized pigment according to one aspect of the present disclosure has technical significance in that it improves the utility of a pigment by solubilizing the pigment as a raw material and improving dyeing affinity and thus allowing dyes with dyeing affinity to be replaced. In this case, the pigment may be an insoluble pigment showing insolubility.

In general, a pigment is a coloring that can color an object and has the property of insolubility, which is insoluble in water, oil, alcohol or the like, unlike the dyes that are soluble in water.

The pigment may be classified by various criteria, and for example, classified into lake pigment and toner pigment, depending on the composition of the pigment.

The lake pigment is a pigment made by adsorbing a water-soluble dye onto an insoluble substrate.

The toner pigment is also a pigment made by adding a precipitating agent such as a metal salt to a water-soluble dye and thus making the water-soluble dye insoluble, as in the lake pigment, but unlike a lake pigment, it is a pigment produced without adding a body pigment.

Since the lake pigment is insoluble and does not actually have a dyeing affinity, but even exhibits properties similar to the dyeing affinity of dyes, it may be more advantageous to use a soluble dye instead of the lake pigment to compensate for the insoluble properties.

However, since the toner pigment is not only insoluble but also has poor dyeing affinity, the dye cannot replace the toner pigment, and thus it is also necessary to solubilize the toner pigment, which is also insoluble, and improve the dyeing affinity.

Therefore, in the cosmetic composition containing the solubilized pigment according to one aspect of the present disclosure, since a pigment may be applied to cosmetic composition instead of the dyes with good solubility and dyeing affinity by solubilizing the pigment and improving the dyeing affinity, it is possible to use a toner pigment as described above as a pigment.

The toner pigment may comprise at least one selected from the group consisting of disodium salt of 4-(2-sulfo-p-tolylazo)-3-hydroxy-2-naphthoic acid; calcium salt of 4-(2- sulfo-p-tolylazo)-3-hydroxy-2-naphthoic acid; and calcium salt of 4-(1-sulfo-2-naphthylazo)-3-hydroxy-2-naphthoic acid.

The disodium salt of 4-(2-sulfo-p-tolyl azo)-3-hydroxy-2-naphthoic acid may be an organic compound represented by the following Formula 1, and may correspond to Red 201 (D&C Red no. 6, CI 15850, Lithol Rubine B, Pigment Red 57).

<Formula 1>

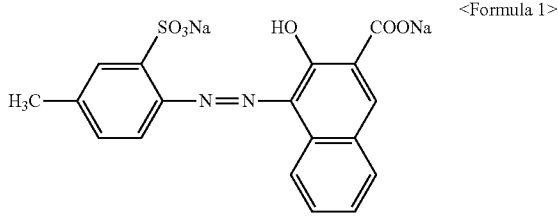

The calcium salt of 4-(2-sulfo-p-tolylazo)-3-hydroxy-2-naphthoic acid may be an organic compound represented by the following Formula 2, and may correspond to Red 202 (D&C Red no. 7, CI 15850:1, Lithol Rubine BCA, Pigment Red 57:1).

<Formula 2>

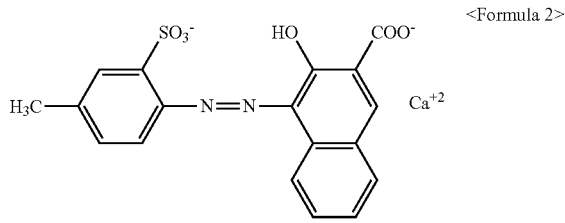

The calcium salt of 4-(1-sulfo-2-naphthylazo)-3-hydroxy-2-naphthoic acid may be an organic compound represented by the following Formula 3, and may correspond to Red 220 (D&C Red no. 34, CI 15880:1, Deep Maroon, Pigment Red 63:1).

<Formula 3>

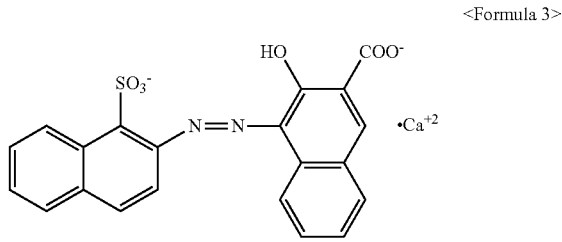

In addition, the pigment may be contained in an amount of 0.1 to 3 wt. % based on the total weight of the cosmetic composition, and specifically, the content of the pigment is 0.1 wt. % or more, 0.3 wt. % or more, 0.4 wt. % or more, or 0.5 wt. % or more, and 2 wt. % or less, 2.5 wt. % or less, 2.8 wt. % or less, or 3 wt. % or less. If the content of the pigment is less than 0.1 wt. %, color may not be developed as desired. If the content of the pigment is more than 3 wt. %, more thickener and acid are used to solubilize the pigment, which increases the preparing cost, or the content of the acid used to solubilize the pigment is relatively lowered, so that the solubility and dyeing affinity may be lowered.

In one aspect of the present disclosure, the pigment dispersing thickener can prevent the pigment particles from agglomerating by dispersing the pigment in the aqueous phase.

The pigment dispersing thickener may comprise at least one selected from the group consisting of ammonium acryloyldimethyltaurate/VP copolymer, hydroxyethyl acrylate/sodium acryloyldimethyltaurate copolymer and polyacrylate-13, and may be ammonium acryloyldimethyltaurate/VP copolymer in terms of compatibility with the insoluble pigment.

In addition, the pigment dispersing thickener may be 0.01 to 2 wt. % based on the total weight of the cosmetic composition, and specifically, the content of the pigment dispersing thickener is 0.01 wt. % or more, 0.05 wt. % or more, or 0.1 wt. % or more, and 1 wt. % or less, 1.5 wt. % or less, or 2 wt. % or less. If the content of the pigment dispersing thickener is less than 0.01 wt. %, it is difficult for the pigment to be completely dispersed in the aqueous phase, so agglomeration phenomenon may occur. If the content of the pigment dispersing thickener is more than 2 wt. %, the viscosity of the cosmetic composition may be high, and the feeling of use may not be good.

In one aspect of the present disclosure, the acid may cause the pigment to be dissolved in a solvent by oxidizing the pigment dispersed in the solvent by the pigment dispersing thickener. At this time, the solubilizer may be additionally added to increase the reaction area between the pigment and the acid, thereby increasing the solubility of the pigment.

The acid may comprise at least one selected from the group consisting of lactic acid, citric acid, ascorbic acid, hyaluronic acid, stearic acid, palmitic acid, lauric acid, and myristic acid, but is not limited to these, as long as it can be used for general cosmetic composition.

In addition, the acid may be contained in an amount of 0.01 to 2 wt. % based on the total weight of the cosmetic composition. Specifically, the content of the acid may be 0.01 wt. % or more, 0.05 wt. % or more, or 0.1 wt. % or more, and 1 wt. % or less, 1.5 wt. % or less, or 2 wt. % or less. If the content of the acid is less than 0.01 wt. %, it may be difficult for the pigment to dissolve in the aqueous phase. If the content of the acid is more than 2 wt. %, the pH is too low, and skin irritation, and thus skin damage may occur.

In one aspect of the present disclosure, the solubilizer increases the reaction area between the pigment and the acid, so that the pigment can be more soluble in the aqueous phase solvent.

The solubilizer may include one or more selected from the group consisting of Polyethylene glycol-60 hydrogenated castor oil, Octyldodeceth-16 and Polysorbate 20.

The solubilizer may be contained in an amount of 0.1 to 5 wt. % based on the total weight of the cosmetic composition, and specifically, the content of the solubilizer may be 0.1 wt. % or more, 0.5 wt. % or more, or 1 wt. % or more, and 3 wt. % or less, 4 wt. % or less, or 5 wt. % or less. If the content of the solubilizer is less than 0.1 wt. %, the effect of improving the solubility of the pigment may be insufficient. If the content of the solubilizer is more than 5 wt. %, as the solubilizer increases, an emulsification reaction of the formulation occurs, so that a change in the formulation such as a suspension of color and an increase in viscosity may occur.

In one aspect of the present disclosure, the stabilizing thickener may function to increase the viscosity of the cosmetic composition to an extent that is easy to use. It can be stabilized by increasing the viscosity of the cosmetic composition.

Since an acid used to dissolve the pigment is contained in the cosmetic composition contains, the stabilizing thickener may be a thickener capable of increasing the viscosity regardless of pH. Specifically, the stabilizing thickener may be a thickener that can function to increase viscosity well even at low pH. The stabilizing thickener may be a salt tolerance thickener and/or a natural thickener that is less affected by pH.

For example, the stabilizing thickener may comprise at least one selected from the group consisting of polyacrylate crosspolymer-6+xanthan gum; polyacrylate-13+xanthan gum; and acrylate copolymer+agar.

In addition, the stabilizing thickener may be contained in an amount of 0.01 to 3 wt. % based on the total weight of the cosmetic composition, and specifically, the content of the stabilizing thickener may be 0.01 wt. % or more, 0.05 wt. % or more, or 0.1 wt. % or more, and 1 wt. % or less, 2 wt. % or less, or 3 wt. % or less. If the content of the stabilizing thickener is less than 0.01 wt. %, the viscosity of the cosmetic composition may not be increased enough to be commercialized. If the content of the stabilizing thickener is more than 3 wt. %, the viscosity of the cosmetic composition is excessively high, so that the feeling of use may not be good.

In one aspect of the present disclosure, the viscosity of the cosmetic composition may be 6,000 to 8,000 cps, specifically, 6,000 cps or more, 6,200 cps or more, or 6,500 cps or more, and 7,500 cps or less, 7,800 cps or less, or 8,000 cps or less. If the viscosity of the cosmetic composition is less than 6,000 cps, it may be difficult to commercialize because the cosmetic composition is not stabilized. If the viscosity of the cosmetic composition exceeds 8,000 cps, the feeling of use of the cosmetic composition may not be good. The viscosity of the cosmetic composition can be controlled by the stabilizing thickener.

In addition, the pH of the cosmetic composition may be 4.5 or less, or 4.0 to 4.5. If the pH of the cosmetic composition is greater than 4.5, since the pigment exists in a simple dispersed state rather than in a dissolved state in the cosmetic composition, the pigment may not exhibit properties similar to dyes, and thus the dyeing affinity of the cosmetic composition may not be good. If the pH of the cosmetic composition is less than 4.0, the pH may be low and there may be irritation to the skin.

In one aspect of the present disclosure, the cosmetic composition containing the solubilized pigment may further comprise functional additives, and/or components which are contained in a general cosmetic composition.

Examples of the functional additives may comprise water-soluble vitamins, oil-soluble vitamins, polymer peptides, polymer polysaccharides, sphingolipids, and seaweed extracts Examples of the components included in the general cosmetic composition may comprise fats and oils, moisturizers, emollients, surfactants, organic powders, ultraviolet absorbers, preservatives, fungicides, antioxidants, plant extracts, pH adjusters, alcohols, pigments, flavorings, blood circulation stimulating materials, cooling sensation agents, anhydrotics, purified water and the like.

As described above, in the cosmetic composition containing the solubilized pigment, the insoluble pigment is solubilized by the acid and included in the cosmetic composition in a dissolved state rather than a simple dispersion, so that the insoluble pigment may exhibit properties similar to dyes.

Therefore, the cosmetic composition containing the solubilized pigment can exhibit a dyeing affinity and a transparent color equal to or higher than the dyes.

In addition, the cosmetic composition containing the solubilized pigment may be used as a variety of color makeup cosmetic composition, as desired, in particular, it can be used as a lip cosmetic composition or cosmetic composition for lip care.

The lip cosmetic composition may comprise cosmetic compositions such as lipstick, lip gloss, or lip pencil.

Preparation Method of Cosmetic Composition Containing Solubilized Pigment

Another aspect of the present disclosure also relates to a method of preparing a cosmetic composition comprising a solubilized pigment, which comprises the steps of (S1) dispersing a pigment in an aqueous phase solvent by introducing the pigment and a pigment dispersing thickener into the aqueous phase solvent; (S2) dissolving the pigment in the aqueous phase solvent by adding an acid to the aqueous phase solvent in which the pigment is dispersed; and (S3) adding a stabilizing thickener to the aqueous phase solvent, in which the pigment is dissolved, thereby stabilizing it.

The types of pigments, pigment dispersing thickeners, acids and stabilizing thickeners used in the above manufacturing method and their contents in cosmetic composition are as described above.

Hereinafter, a method of preparing the cosmetic composition containing the solubilized pigment according to another aspect of the present disclosure will be described in more detail for each step.

In another aspect of the present disclosure, in step (S1), the pigment and the pigment dispersing thickener may be added to the aqueous phase solvent to disperse the pigment in the aqueous phase solvent.

The aqueous phase solvent may be at least one selected from the group consisting of water, glycerin, methyl alcohol, and ethyl alcohol, but is not limited thereto, as long as it is an aqueous phase solvent that can be generally used in cosmetic compositions.

The pigment and the pigment dispersing thickener are added to the aqueous phase solvent, the pigment is contained in a dispersed state in the aqueous phase solvent whose viscosity is increased to a low viscosity. At this time, the aqueous phase solvent may be increased in viscosity to a low viscosity enough to disperse the pigment. Specifically, the low viscosity may be 2000 to 5000 cps.

In another aspect of the present disclosure, in step (S2), the pigment may be dissolved in the aqueous phase solvent by adding the acid to the aqueous phase solvent in which the pigment is dispersed. In addition, a solubilizer may be additionally added to improve the solubility of the pigment.

The acid can dissolve the pigment in the aqueous phase solvent whose viscosity is increased to the low viscosity by oxidizing the pigment. At this time, the aqueous phase solvent whose viscosity is increased to the low viscosity can be made to be less than pH 4.5, so that the pigment can be sufficiently dissolved. Accordingly, the final prepared cosmetic composition may also have a pH of 4.5 or less.

In addition, a solubilizer may be additionally added together with the acid to better dissolve the pigment in the aqueous phase solvent.

The solubilizer may further improve the solubility of the pigment by maximizing the reaction area between the pigment and the acid.

At this time, the better the pigment is dissolved in the aqueous phase solvent, the more transparent the aqueous phase solvent is, so it can be confirmed whether the pigment is dissolved.

In another aspect of the present disclosure, in step (S3), it can be stabilized by adding the stabilizing thickener to the aqueous phase solvent in which the pigment is dissolved.

The stabilizing thickener may increase the viscosity of the aqueous phase solvent in which the pigment is dissolved, which is obtained in the step (S2), so as to increase the viscosity to such an extent that it can be actually used as a cosmetic composition and thus to prepare a formulation of the stabilized cosmetic composition.

Hereinafter, the present invention will be described in more detail through examples, but the following examples are not intended to limit the scope of the present invention, and these examples may be interpreted to help understand the present invention.

In the following Examples and Comparative Examples, cosmetic compositions were prepared according to the composition as shown in Table 1 below.

Example 1

A cosmetic composition was prepared according to the composition as described in Table 1 below.

The pigment and the pigment dispersing thickener were added to the aqueous phase solvent to disperse the pigment in the aqueous phase solvent.

The acid and the solubilizer were added to the aqueous phase solvent, in which the pigment was dispersed, to dissolve the pigment in the aqueous phase solvent.

The pigment was solubilized by adding the stabilizing thickener to the aqueous phase solvent and thus stabilizing it. At this time, butylene glycol, a preservative and a flavoring, which are moisturizing agents as additives, were added together, and mixed with an Agi mixer at 40° C. to prepare a cosmetic composition.

TABLE 1

| Unit: wt. % | | Example 1 | Comparative Example 1 | Comparative Example 2 |
| --- | --- | --- | --- | --- |
| Pigment | disodium salt of 4-(2-sulfo-p-tolylazo)-3-hydroxy-2-naphthoic acid | 0.5 | 0.5 | 0 |
| Dye | Red 227 | 0 | 0 | 0.5 |
| Pigment dispersing thickener | ammonium acryloyl dimethyl taurate/VP copolymer | 0.4 | 0.4 | 0.4 |
| Acid | lactic acid | 0.2 | 0 | 0.2 |
| Solubilizer | Polyethylene glycol-60 hydrogenated castor oil | 2 | 2 | 2 |
| Stabilizing thickener | polyacrylate crosspolymer-6 + xanthan gum | 0.6 | 0.6 | 0.6 |
| Aqueous phase solvent | purified water glycerin | To 100 15 | To 100 15 | To 100 15 |
| Butylene glycol | | 1 | 1 | 1 |
| Preservatives | | 1 | 1 | 1 |
| Flavorings | | 0.2 | 0.2 | 0.2 |

Comparative Example 1

A cosmetic composition was prepared in the same manner as in Example 1, except that the acid was not added during solubilization of the pigment.

Comparative Example 2

A cosmetic composition for lips was prepared in the same manner as in Example 1, except that a dye was used instead of the pigment.

Experimental Example 1: Evaluation of the Difference in Pigment Appearance Depending on the Degree of Acidification of the Pigment FIG. 1 is a photograph showing the color of the pigment depending on the pH controlled by the acid added to the aqueous phase solvent in which the pigment is dispersed in Example 1, which shows the change in color represented by the pigment as the pH is lowered while gradually adding the acid to the aqueous phase solvent in which the pigment is dispersed in Example 1. The case of pH 4.14 is Example 1.

Referring to FIG. 1, the aqueous phase solvent containing the pigment appears to be dark and transparent in color at a slightly acidic pH of 4.14. From this, it can be seen that the pigment was dissolved.

FIG. 2 is a photograph showing the appearances of the cosmetic compositions prepared in Example 1 and Comparative Example 1, respectively.

Referring to FIG. 2, it can be seen that the appearance of Comparative Example 1 is opaque, while the appearance of Example 1 is transparent.

In Comparative Example 1, an insoluble pigment is contained in the cosmetic composition in a simple dispersed state in the aqueous phase solvent, while in Example 1, an insoluble pigment is solubilized and contained in a dissolved state in a cosmetic composition. From this, it can be seen that the appearance varies depending on the state of the pigment contained in the cosmetic composition.

At this time, the case as in Example 1 is called a solubilized formulation, and the solubilized formulation refers to a formulation in which an insoluble substance that is not soluble in water is dissolved in water and thus is in a thermodynamically stable state, and separation between the aqueous phase and the oil phase does not occur therefrom.

The case as in Comparative Example 1 is called an emulsion formulation, and the emulsion formulation is in the form, in which an insoluble material is uniformly dispersed by forming an interfacial film, and is thermodynamically unstable and thus separation between the aqueous and oil phases can occur therefrom.

Also, in addition to the solubilized formulation and emulsion formulation, the aqueous dispersion formulation means a formulation in which no water-insoluble substance is present or a very small amount thereof is dispersed.

Experimental Example 2: Experiment of Dyeing Affinity

FIG. 3 is a photograph showing the experimental results of dyeing affinity of the cosmetic compositions prepared in Example 1, Comparative Example 1 and Comparative Example 2, respectively.

For the experiment of dyeing affinity, the cosmetic compositions prepared in Example, Comparative Example 1 and Comparative Example 2 were applied to the inner skin of the subject's arm with a finger, and wiped with tissue after 3 minutes, and thereafter, the skin was visually observed to determine dyeing affinity.

Referring to FIG. 3, Comparative Example 1 is a cosmetic composition containing pigment in a dispersed state, and as a result of visual observation, it can be seen that the dyeing affinity for the skin is poor.

On the other hand, Example 1 is a cosmetic composition containing pigment in a dissolved state, and Comparative Example 2 is a cosmetic composition containing a dye. As a result of visual observation, it was confirmed that the degree of dyeing on the skin is similar to each other.

In the above, although the present invention has been described with reference to limited examples and drawings, the present invention is not limited thereto, and it will be apparent to those of ordinary skill in the art to which the present invention pertains that various modifications and variations are possible within the technical scope of the present invention and within the equality of the claims to be described below.

What is claimed is:

1. A lip cosmetic composition comprising
    a toner pigment selected from the group consisting of disodium salt of 4-(2-sulfo-p-tolylazo)-3-hydroxy-2-naphthoic acid and calcium salt of 4-(2-sulfo-p-tolylazo)-3-hydroxy-2-naphthoic acid in an amount of 0.1 to 3 wt. %;
    a first thickener in an amount of 0.01 to 2 wt %;
    an acid in an amount of 0.01 to 2 wt %; and
    a solubilizer in an amount of 0.1 to 5 wt %;
    a second thickener in an amount of 0.01 to 3 wt %;
    water; and
    glycerin,
    wherein the first thickener comprises one or more selected from the group consisting of ammonium acryloyldimethyltaurate/VP copolymer, hydroxyethyl acrylate/sodium acryloyldimethyltaurate copolymer, and polyacrylate-13;
    wherein the second thickener comprises one or more selected from the group consisting of polyacrylate crosspolymer-6+xanthan gum; polyacrylate-13+xanthan gum; and acrylate copolymer+agar; and
    wherein the lip cosmetic composition is transparent.

2. The lip cosmetic composition according to claim 1, wherein the acid comprises one or more selected from the group consisting of lactic acid, citric acid, ascorbic acid, hyaluronic acid, stearic acid, palmitic acid, lauric acid, and myristic acid.

3. The lip cosmetic composition according to claim 1, wherein the formulation of the lip cosmetic composition is selected from the group consisting of emulsion, gel, and cream.

4. The lip cosmetic composition according to claim 1, wherein the viscosity of the lip cosmetic composition is 6,000 to 8,000 cps.

5. The composition of claim 1, further comprising butylene glycol.

6. The composition of claim 1, further comprising preservatives.

7. The composition of claim 1, further comprising flavorings.

8. A method of preparing the lip cosmetic composition of claim 1, comprising:
    (S1) dispersing a toner pigment selected from the group consisting of disodium salt of 4-(2-sulfo-p-tolylazo)-3-hydroxy-2-naphthoic acid and calcium salt of 4-(2-sulfo-p-tolylazo)-3-hydroxy-2-naphthoic acid in an aqueous phase solvent by introducing the toner pigment and a first thickener into an aqueous phase solvent comprising water and glycerin;
    (S2) adding an acid and a solubilizer to the composition obtained in (S1) to obtain an aqueous solution containing said toner pigment; and
    (S3) adding a second thickener to the aqueous phase solution obtained in (S2), thereby stabilizing the aqueous solution,
    wherein the first thickener comprises one or more selected from the group consisting of ammonium acryloyldimethyltaurate/VP copolymer, hydroxyethyl acrylate/sodium acryloyldimethyltaurate copolymer, and polyacrylate-13; and
    wherein the second thickener comprises one or more selected from the group consisting of polyacrylate crosspolymer-6+xanthan gum; polyacrylate-13+xanthan gum; and acrylate copolymer+agar.

* * * * *